(12) United States Patent
Shmuylovich et al.

(10) Patent No.: US 7,749,763 B2
(45) Date of Patent: Jul. 6, 2010

(54) KITS AND METHODS FOR EVALUATING HAIR

(75) Inventors: Gregory Shmuylovich, Springfield, NJ (US); Henry T. Kalinoski, Doylestown, PA (US); Robert Picone, New Providence, NJ (US); Jacob Rosen, Scotch Plains, NJ (US); Michael A. Kravetz, Leonardo, NJ (US)

(73) Assignee: L'Oreal S.A., Paris (FR)

( * ) Notice: Subject to any disclaimer, the term of this patent is extended or adjusted under 35 U.S.C. 154(b) by 103 days.

(21) Appl. No.: 12/057,676

(22) Filed: Mar. 28, 2008

(65) Prior Publication Data

US 2008/0241854 A1 Oct. 2, 2008

Related U.S. Application Data

(60) Provisional application No. 60/912,188, filed on Apr. 17, 2007, provisional application No. 60/908,719, filed on Mar. 29, 2007.

(51) Int. Cl.
*G01N 33/48* (2006.01)
*G01N 33/52* (2006.01)
*G01N 33/20* (2006.01)
*G01N 21/77* (2006.01)

(52) U.S. Cl. .............. 436/63; 436/73; 436/84; 436/164; 436/169; 436/174; 436/175; 422/55; 422/56; 422/61; 422/82.05; 435/7.1

(58) Field of Classification Search .................. 436/63, 436/73, 79–81, 84, 86, 164, 166, 169, 174, 436/177, 175; 422/55, 56, 61, 82.05; 435/7.1

See application file for complete search history.

(56) References Cited

U.S. PATENT DOCUMENTS

| 4,510,250 A | * | 4/1985 | Kabacoff et al. ............... 436/63 |
| 4,665,741 A | | 5/1987 | Kabacoff et al. |
| 5,131,417 A | * | 7/1992 | Zaias et al. .................. 132/204 |
| 5,290,519 A | | 3/1994 | Barr-Or et al. |

(Continued)

FOREIGN PATENT DOCUMENTS

DE  44 32 854 C1  3/1996

(Continued)

OTHER PUBLICATIONS

Merckoquant Lead Test: Instructions for use sheet, URL=http://www.merck-chemicals.com/chemat/en US/Merck-International-Site/USD/ViewProductDocuments-File?ProductSKU=MDACHEM-110077&DocumentType=Pi&DocumentID=7394.ProNet&DocumentSource=Pronet, date unknown.

*Primary Examiner*—Maureen M Wallenhorst
(74) *Attorney, Agent, or Firm*—Oblon, Spivak, McClelland, Maier & Neustadt, L.L.P.

(57) ABSTRACT

The invention relates to kits and methods for analyzing hair, particularly for determining the amount of damage to hair, including placing hair into a solution containing at least one metal ion so that an amount of the metal ion is attached to the hair, removing the hair from the solution, determining the amount of metal ion attached to the hair, and determining the amount of damage to the hair based upon the amount of metal ion attached to the hair.

21 Claims, 5 Drawing Sheets

U.S. PATENT DOCUMENTS 5,461,925 A * 10/1995 Nguyen et al. ................. 73/789
5,552,297 A     9/1996 Wong et al.
6,672,143 B2 *  1/2004 Schulze zur Wiesche
                        et al. .......................... 73/64.53
6,730,493 B1 *  5/2004 Schwan-Jonczyk et al. ... 435/23
6,817,222 B2 * 11/2004 Day et al. ......................... 73/9

7,261,000 B2 *  8/2007 Sherman et al. ............... 73/789

FOREIGN PATENT DOCUMENTS

JP        2002107362   *  4/2002
WO     WO 2006/089338     8/2006

* cited by examiner

Nickel Probe Measurements Plotted against Alkaline Solubility Values for the Same Nine Caucasian Hair Samples

KITS AND METHODS FOR EVALUATING HAIR

CROSS-REFERENCE TO PRIOR APPLICATIONS

This application claims priority to U.S. provisional applications 60/908,719 filed Mar. 29, 2007 and 60/912,188 filed Apr. 17, 2007, the entirety of which is hereby incorporated by reference.

FIELD OF THE INVENTION

The present invention generally relates to kits and methods for analyzing or evaluating hair, particularly for determining the amount of damage to hair, comprising placing hair into a solution comprising at least one metal ion so that an amount of the metal ion is attached to the hair, removing the hair from the solution, determining the amount of metal ion attached to the hair, and determining the amount of damage to the hair based upon the amount of metal ion attached to the hair. Such kits and methods allow for rapid, quantitative analysis of hair, particularly determination of hair damage.

DISCUSSION OF THE BACKGROUND

Hair damage is characterized by dull looking, brittle fibers which tend to break easily and have increased porosity. In addition, cuticle cells tend to be uplifted indicating hair shaft damage with the presence of split ends.

The damage is caused by three types of insult: mechanical, chemical and environmental. Too frequent or excessive brushing or combing causes shaft damage, split ends and uplifted cuticle cells. Over-vigorous chemical treatments from perming, dying, bleaching or too alkaline shampoos cause hair protein hydrolysis and oxidation of cystine linkages. Environmental insult or hair "weathering" from climatic exposure, sunlight, air pollutants, wind, seawater and chlorinated swimming pool water cause photo oxidative splitting of cystine linkages, initiate free radicals detrimental to the protein matrix and increase porosity of the cuticle.

To better understand the extent to which hair has been damaged by such factors or treatments, or to evaluate the extent to which hair damage has been repaired by ameliorative procedures, objective measurements of hair properties are preferably made. These measurements have been mechanical such as, for example, measuring the hair's resistance to breakage, or they have been chemical in nature such as, for example, measuring the hair's solubility in selected media. Such measurements often require an extensive amount of time and/or a large amount of hair to complete. Further, these measurements may require specific instrumentation only found in specialized laboratories and, thus, are not capable of being conducted at or near a point of hair treatment.

Others have tried to evaluate hair damage using absorption of copper by hair. In these efforts, hair damage was indirectly determined by analyzing the amount of metal remaining in a treatment solution after the solution was exposed to a hair sample. By determining the amount of metal remaining in the solution, an inference was made as to how much metal was absorbed by the hair. This amount of metal was presumed to be related to the amount of hair damage. Unfortunately, such indirect measurements may not have the accuracy and precision required to differentiate the amount of damage in closely related hair samples. Moreover, such indirect measurements may be complicated by contamination: that is, contributions to the solution's metal content by metal already present in the hair may skew the results, particularly when more commonly occurring metals such as copper are used. Finally, such indirect measurements may not be accurate owing to the loss of metal ions to other locations such as, for example, the containers used for the treatment process, thereby skewing the results.

For example, previous work by Tripathi and Tomaszewicz (1981) describes the use of a copper solution to evaluate hair damage and the indirect measurement of the residual copper solution to determine the amount of copper uptake. This indirect measurement was conducted using a laboratory-based titration. A similar approach is described by Kabacoff and Govil (1985) and by Kabacoff et al. (1987) which use copper absorption by hair and the indirect measurement of the resulting copper solution. In these efforts, the copper concentration is determined by measuring the color intensity of the resulting solution. The color intensity is compared to a physical color standard (color chart, color tube or glass slides), thereby requiring a subjective evaluation. More objective measurements of the color intensity, such as a filter photometer or an impedance measurement, can also be performed. However, such measurements do not result in an objective determination of the actual amount of metal present, only the evaluation of the color of the solution.

Furthermore, existing methods of hair damage evaluation are typically not sensitive enough to provide reliable results for damage to hair resulting from all kinds of hair treatments, particularly in view of the fact that cosmetic companies have been developing gentler hair products which, when used, inflict less damage to hair than the previous generation of products.

Thus, there is a need in the art to have sensitive, direct, objective measurement procedures for determining the amount of damage to hair, procedures which are easy to employ, use a small amount of hair, require a short amount of time, and/or utilize uncomplicated equipment which allows the procedures to be practiced at or near a point of hair treatment (such as, for example, a beauty or hair salon).

SUMMARY OF THE INVENTION

The present invention relates to methods for determining the amount of damage to hair, comprising placing hair into a solution comprising at least one type of metal ion so that an amount of the metal ion is attached to the hair, removing the hair from the solution, determining the amount of metal ion attached to the hair, and determining the amount of damage to the hair based upon the amount of metal ion attached to the hair.

The present invention also relates to kits for analyzing hair comprising a solution comprising (a) at least one type of metal ion, (b) a digesting agent in an amount sufficient to release the metal ion from hair after the metal ion has become attached to the hair when the hair is placed into the solution, and (c) means for determining the amount of metal ion attached to the hair. The kits can further comprise means for determining the amount of damage to the hair based upon the amount of metal ion attached to the hair.

It is to be understood that both the foregoing general description and the following detailed description are exemplary and explanatory only, and are not restrictive of the invention.

DETAILED DESCRIPTION OF THE INVENTION

Figure 1:
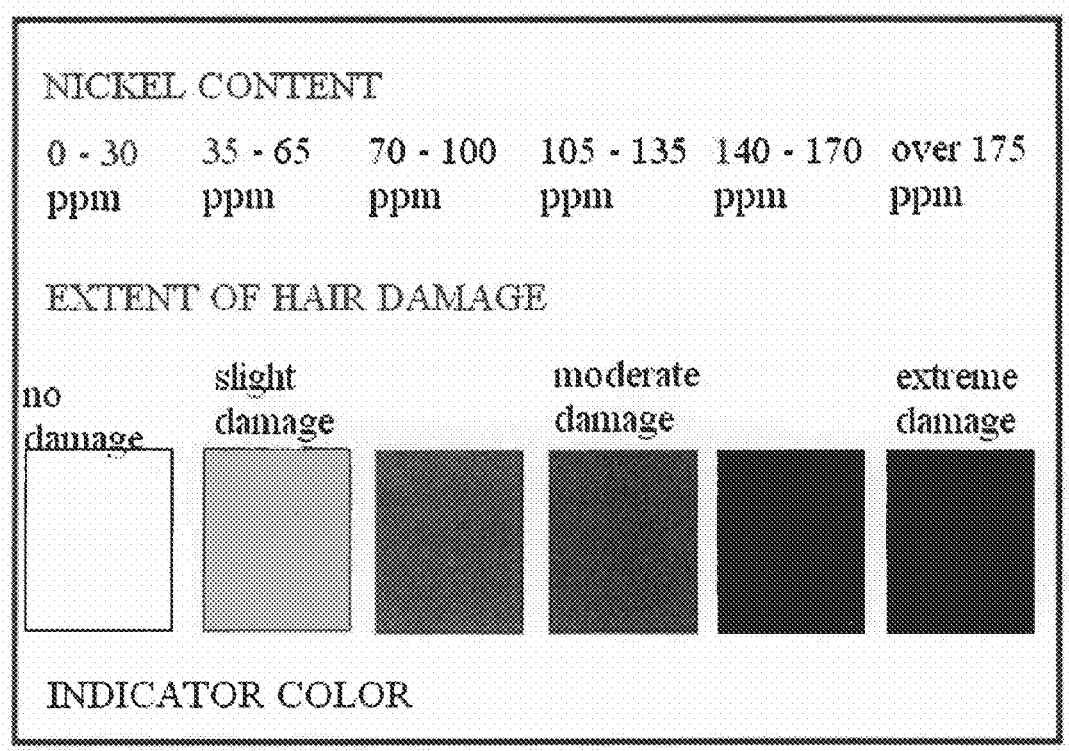
FIG. 1 is an example of a chart for correlating the amount of hair damage to the amount of metal ion attached to the hair.

As used herein, the expression "at least one" means one or more and thus includes individual components as well as mixtures/combinations.

The compositions and methods of the present invention can comprise, consist of, or consist essentially of the essential elements and limitations of the invention described herein, as well as any additional or optional ingredients, components, or limitations described herein or any otherwise useful ingredient, component or limitation typically found in analytical compositions or methods.

Methods of Determining Hair Damage

According to the present invention, methods for determining the amount of damage to hair are provided. These methods comprise placing hair into a solution comprising at least one type of metal ion so that an amount of the metal ion is attached to the hair, removing the hair from the solution, determining the amount of metal ion attached to the hair, and determining the amount of damage to the hair based upon the amount of metal ion attached to the hair.

While not wishing to be bound to any particular theory, it is believed that metal ions can attach to hair, prior to and after damage, primarily through ion exchange/absorption, and that the uptake of cationic metals can be made to be proportional to the amount of hair damage.

Thus, by determining the amount of metal ion attached to hair, the amount of hair damage can be determined objectively and quantitatively.

According to the present invention, the hair being analyzed for damage can be any type of hair. For example, the hair can be that of a human (male or female) or of an animal (for example, horse, dog, cat, etc.). The hair can be from any location on the human or animal such as, for example, eyebrows, eyelashes, or the head. Preferably, the hair being analyzed is from the head of a human.

In accordance with the present invention, the hair being analyzed is placed into a solution. As used herein, "solution" means a liquid (non-solid) composition.

Further in accordance with the present invention, the solution comprises at least one type of metal ion and at least one solvent which is compatible with and solubilizes the at least one type of metal ion. Preferred solvents include, but are not limited to, water, alcohols such as, for example, ethanol, propanol, butanol, etc., ketones such as acetone, and mixtures thereof.

According to preferred embodiments, the solution is aqueous and has a pH ranging from about 6.5 to about 7.5, most preferably about 7.0. The desired pH of the solution can be achieved by adding a pH adjusting agent to the solution in an amount sufficient to raise or lower the pH to the desired level. Suitable pH adjusters include known acidifying agents such as, for example, hydrochloric acid or sulfuric acid and known alkalinizing agents such as, for example, ammonia or alkali carbonate/bicarbonates.

In accordance with the present invention, many types of metal ion may be used. For example, metal ions in the +2 charge state and +3 charge state can be used. Suitable types of metal ions include, but are not limited to, gold, silver, platinum, iron, copper, zinc, nickel, and mixtures thereof. Preferably, metal ions are in the +2 charge state and/or are transition metal ions. According to particularly preferred embodiments, the metal ion is an ion which is not generally present in the food supply, environment and/or not generally present in commercially available beauty or cleansing products. Such ions are referred to herein as "non-contamination metal ions"—owing to the lack of such ions in the food supply, environment and/or commercially available products, little or no contamination of such ions would exist when using such ions in the invention methods. For example, metal ions such as nickel and manganese, are not typically found in products and/or in the environment and, thus, would constitute acceptable non-contamination metal ions. In contrast, copper, calcium, magnesium, phosphorous, sodium, potassium, iron and zinc ions are more prevalent in the food supply, beauty products and/or the environment, meaning that a greater risk of contamination (and, thus, a greater risk of affecting the results of the invention methods) might exist. Preferred non-contamination metal ions include, but are not limited to, nickel and manganese and mixtures thereof. Particularly preferred metal ions are nickel ions, particularly nickel 2+ ions.

According to the present invention, the solution comprises at least one type of metal ion in an amount sufficient to allow a detectable amount of the metal ion to attach to the hair added to the solution. Thus, the amount of metal ion in solution may vary based upon the amount of hair added to the solution. In preferred embodiments, the amount of at least one type of metal ion present in the solution is on the order of hundreds of parts per million (ppm), for example between 100 and 1000 ppm. More preferably, the metal ion is present in an amount between 200 and 600 ppm, with an amount between 350 and 450 ppm being most preferred. The amount of hair added to the solution is preferably less than one gram of hair, more preferably less than 0.5 grams of hair, with 0.1-0.3 grams being the preferred range. Preferably, both the concentration of metal ion and the amount of hair being analyzed are known when practicing the invention methods.

In accordance with the present invention, the hair remains in the solution for a sufficient amount of time to allow the metal ions to attach to the hair. Preferably, the hair remains in the solution for at least 15 minutes, more preferably for at least 30 minutes, and most preferably for at least 45 minutes. While the hair is in the solution, the solution can be agitated (for example, swirling), if desired.

In accordance with the present invention, at least one type of metal ion is attached to the hair through any suitable mechanism. Preferred mechanisms include, but are not limited to, ion exchange, absorption, adsorption, bonding and binding. The most preferred attachment mechanism is ion exchange/absorption.

According to the present invention, after hair has been placed into the solution and metal ion has attached to the hair, the hair is removed from the solution. Any suitable removal methods can be used to remove the hair from the solution such as, for example, removing the hair from the solution with forceps, tweezers or some other similar instrument, pouring the solution over filter paper or sieve so that the solution runs through the filter paper/sieve but the hair does not, etc.

According to preferred embodiments, after the hair has been removed from solution, the hair is rinsed with a rinsing solution to remove excess or unbound metal. Preferably, the rinsing solution is the same or substantially similar to the solution from which the hair has been removed except that the rinsing solution does not contain any metal ion. Most preferably, the hair is rinsed between 3 and 5 times, with 4 times being most preferred.

Further in accordance with preferred embodiments, after rinsing, the hair is allowed to dry. Preferably, the hair is heated during drying. According to preferred embodiments, the hair is heated at a temperature from about 80° C. to about 140° C., with about 110° C. being most preferred, for about 10 to about 20 hours, with about 16 hours being most preferred. Of course, it is to be understood that the temperature at which the hair is dried is somewhat inversely proportional to the length of time it is dried: the higher the temperature, the less time will be needed for drying, and vice versa.

In accordance with the present invention, after the hair has been removed from the solution, the amount of metal ion attached to the hair is determined. According to preferred embodiments, determining the amount of metal ion attached to the hair is a two-step process. The first step separates the metal ion from the hair (or de-attaches the metal ion from the hair). The second step determines the amount of metal ion which has been released (or de-attached) from the hair.

According to preferred embodiments, the metal ion is separated from the hair by treating the hair with a digesting agent in an amount sufficient to release the metal ion from the hair. Any suitable digesting agent (that is, an agent that degrades keratinous material such as hair) can be used in accordance with the present invention as long as it causes substantially all of the metal ion to be released from or separated from the hair. Preferably, the digesting agent is in a solution which comprises, in addition to the digesting agent, at least one compatible solvent with the purpose of solublizing the mixture, especially the metal ions.

Acceptable digesting agents include, but are not limited to, acids, hydroxyacids, salts of hydroxyacids, oxidizing agents, enzymes, and mixtures thereof.

Acceptable acids include acids such as hydrochloric acid, sulfuric acid and nitric acid. Nitric acid is a particularly preferred acid.

Acceptable hydroxyacids include derivatives of alpha or beta hydroxyacids. Preferred hydroxyacid derivatives include, but are not limited to, sulfur-containing derivatives such as, for example, thioglycolic acid, thiolactic acid, thiocitric acid, thiomalic acid, thiosalicylic acid, and mixtures thereof. Particularly preferred sulfur alpha hydroxyacids are thioglycolic acid and thiolactic acid.

Acceptable salts of hydroxyacids include compounds containing a cation and an anion corresponding to a derivative of an alpha or beta hydroxyacid. Preferred anions corresponding to a hydroxyacid derivative include, but are not limited to, the anions corresponding to sulfur-containing derivatives such as, for example, thioglycolic acid, thiolactic acid, thiocitric acid, thiosalicylic acid and thiomalic acid. Preferred cations include, but are not limited to, alkali metals (sodium, potassium, etc.), alkaline earth metal (calcium, magnesium, etc.) and ammonium. Particularly preferred salts of sulfur alpha hydroxyacids include sodium thioglycolic acid (sodium thioglycolate), potassium thioglycolic acid (potassium thioglycolate), sodium thiolactic acid (sodium thiolactate), potassium thiolactic acid (potassium thiolactate), ammonium thiolactic acid (ammonium thiolactate), ammonium thioglycolic acid (ammonium thioglycolate), ethanolamine thioglycolic acid (ethanolamine thioglycolate), ethanolamine thiolactic acid (ethanolamine thiolactate), isooctyl thioglycolic acid (isooctyl thioglycolate), isooctyl thiolactic acid (isooctyl thiolactate), magnesium thioglycolic acid (magnesium thioglycolate), magnesium thiolactic acid (magnesium thiolactate), strontium thioglycolic acid (strontium thioglycolate), strontium thiolactic acid (strontium thiolactate), and mixtures thereof.

Acceptable digesting agents include, but are not limited to, oxidizing agents such as peroxides and halogenates, halogenides and halogenites. A particularly preferred digesting agent of the peroxide type is hydrogen peroxide.

Other acceptable digesting agents are enzymes. Suitable enzymes include, but are not limited to, keratinases. Keratinases are generally proteases produced by insects or microorganisms. For example, suitable examples of keratinases include those from the dermatophytic genera *Microsporum* or *Trichophyton* as well as from bacteria of the genera *Bacillus* or *Streptomyces*.

Preferably, the digesting agent is used in an amount sufficient to cause substantially all of the metal ion to be released from or separated from the hair. When the digesting agent is in a solution, the amount of digesting agent present ranges from about 1% to about 90% by weight of the total weight of the solution, more preferably from about 5% to about 70% of the total weight of the solution, more preferably from about 10% to about 50% of the total weight of the solution, and most preferably from about 20% to about 40% of the total weight of the solution, including all ranges and subranges therebetween. In accordance with the present invention, the hair to which the metal ion has attached remains in the solution for a sufficient amount of time to allow the metal ions to de-attach from the hair. One of ordinary skill in the art will recognize that the amount of digesting agent present will depend upon several factors such as the amount of hair being analyzed, the strength (enzymatic activity or reducing/oxidizing activity) of the digesting agent, the time for which the digesting agent is exposed to the hair being analyzed, etc. Preferably, the hair remains in the solution for at least 1 minute, more preferably for at least 10 minutes, and most preferably for at least 30 minutes. According to preferred embodiments, digestion occurs at an elevated temperature (that is, greater than room temperature) such as, for example, between 30° C. and 95° C. via a heating unit such as a conventional oven, a microwave oven or a heating block, although digestion can also occur at or below room temperature, if desired. It is important that after digestion which removes the metal ion from the hair, the metal ion remains in solution for the analysis.

According to preferred embodiments, once the metal ion has been separated from the hair, the amount of metal ion released from the hair is determined. Preferably, the amount of metal ion is determined by reacting the released metal ion with a dye or other chemical agent to form a colored complex having an intensity and then determining the intensity of the colored complex. Preferably, the metal ions and dyes are chosen such that the colored complexes formed are in direct proportion to the amount of metal ion present in a sample or solution. The intensity of the color of these complexes can be a sensitive, direct, objective measurement of the amount of metal ion present in a sample or solution.

Thus, in accordance with preferred embodiments of the present invention, after the hair sample being analyzed has been added to a solution containing the digesting agent to release the metal ion from the hair sample, the released metal ion is then reacted with a dye or other chemical agent to form a colored complex having an intensity. Preferably, the metal ion is reacted with the dye or other chemical agent in the solution for at least 15 seconds, more preferably for at least 30 seconds, and most preferably for at least 45 seconds. Also preferably, the amount of dye or other chemical agent present is in excess of the amount of metal ion present to facilitate substantially complete binding of the metal ion.

Suitable dyes or other chemical agents for use in the invention methods include, but are not limited to, compounds which have binding specificity for the metal ion attached to the hair. Suitable examples of such dye or other chemical agent/metal ion relationships include, but are not limited to, Methyl calcein blue, Murexide, Fast Sulphon Black, Eriochrome Red B, Calcein, Calcon, Calmagite, Eriochrome Black T, Eriochrome blue-black B, Eriochrome blue SE, Hydroxynaphthol blue, Methylthymol blue, Phthalein purple, Pyrogallol red, 3,3'-dimethylnaphthidine, Chromazurol S, Naphthol Green B, 1-(2-pyridilazo)-2-naphthol (PAN), xylenol orange and zincon reagent. One skilled in the art would readily be able to select appropriate dyes or other chemical agents based upon the metal ion attached to the hair and the available dyes or chemical agents which bind with such ions. Particularly preferred agents are those agents which bind with nickel 2+ ions such as, for example, Pyrocatecholsulfonephthalein (pyrocatechol violet), murexide (monoammonium salt of [(hexahydro-trioxo-pyrimidinyl)-imino]-pyrimidine trione), pyridylazo-naphthol (PAN), thiazolylazo-naphthol (TAN), cyclohexanedionedioxime (Nioxime), hydrated furildioxime (Alpha Furildioxime), diglyme (diethylene glycol dimethyl ether), Oxine, Phenanthroline, and Dimethylglyoxime.

According to one embodiment of the present invention, the dye or other chemical agent is in a solution containing the digesting agent at the time the hair is added to it. According to another embodiment, the dye or other chemical agent is added to the solution after the hair has been added to the solution and the metal has been separated from the hair (or in the process of being separated from the hair).

According to present invention, the metal ion and the dye or chemical agent bind to form a "metal dye complex." The dye or other chemical agent changes color when the compound reacts with the metal ion in solution.

According to preferred embodiments, the intensity of the color of the metal dye complex is directly measured from the solution.

According to other preferred embodiments, the amount of metal ion is determined by reacting the released metal ion in solution with a test strip comprising a dye or other chemical agent to form the metal dye complex on the test strip. In accordance with this embodiment, suitable test strips are commercially available for a range of metals and show low detection limits (on the order of 10 to 200 ppm) for selected metals. Typically, these test strips are used for analyzing water, wastewater, electroplating baths and cooling lubricants. Specific examples of such test strips include, but are not limited to, test strips marketed in connection with the Reflectoquant system commercialized by EMScience. Suitable test strips also include strips based on nanoparticles of dye particles such as those disclosed in Yukiko et al., Ang. Chemie Intl. Edition, vol 45, 6, 913-916, 12/2005, the entire contents of which is hereby incorporated by reference.

The intensity of the color of the complex in solution or on the test strip can be measured in any suitable manner. For example, the intensity can be read and determined directly by eye or by using a reflectometer. The intensity of the color is directly proportional to the amount of metal ion in the solution or on the test strip.

In accordance with the present invention, once the amount of metal ion attached to the hair has been determined, the amount of damage to the hair based upon the amount of metal ion attached to the hair is determined. Because the amount of hair damage is proportional to the amount of metal ion attached to the hair, the amount of hair damage can be determined based on the amount of metal ion attached to the hair. Such determination can be facilitated by correlation aids such as, for example, a color chart, written instructions or charts, and/or videographic information (including CD or DVD based information) which reflect the visible color intensities related to various concentrations of metal ions and, thus, make it possible to correlate the metal ion concentration to the amount of hair damage.

For example, FIG. 1 is an example of a chart that could be produced for use as such a correlation aid. Such a chart could be produced by analyzing hair samples of known condition or damage using the analytical methods described herein. Hair of known condition/damage can be obtained from a variety of sources and the extent of damage can be established through acceptable techniques such as, for example, those disclosed below in the examples. The nickel content of these known hair samples, after treatment according to the present invention, is then determined using any acceptable technique, such as atomic absorption spectroscopy (AAS), inductively-coupled plasma spectroscopy (ICP), other spectroscopic methods, spectrophotometric methods, colorimetric measurements or through use of the appropriate nickel-selective test strip. The color chart can be prepared by an evaluation of the solutions obtained from the digestion of the treated hair and the results obtained through use of the test strips or appropriate metal-dye complex. The condition of hair of unknown quality can then be determined by comparison with such a correlation aid.

Kits for Analyzing or Evaluating Hair

According to the present invention, kits for analyzing or evaluating hair are also provided. According to preferred embodiments, these kits contain sufficient elements to allow the practice of the methods for analyzing or evaluating hair discussed above. Thus, these kits can contain elements such as, for example, tweezers, forceps, filter paper, etc. for removing hair from solution; all necessary containers, jars or vials for preparing and analyzing samples; all ingredients necessary to practice the invention methods such as, for example, metal ions, digesting agents, solvents, etc., preferably separately and individually packed; and/or cleansing materials such as disinfecting wipes.

In accordance with this embodiment, kits for analyzing hair comprising (a) a solution comprising at least one metal ion; (b) a digesting agent in an amount sufficient to release the metal ion from hair after the metal ion has become attached to the hair when the hair is placed into the solution; and (c) means for determining the amount of metal ion attached to the hair are provided. The solution, metal ion, and digesting agent in these kits are discussed above. The means for determining the amount of metal ion attached to the hair preferably comprises a dye or other chemical agent which binds the metal ion, which can either be in solution or part of a test strip. This means preferably further comprises a reflectometer.

According to preferred embodiments, the kits further comprise means for determining the amount of damage to the hair based upon the amount of metal ion attached to the hair. This means preferably comprises a color chart, written instructions or charts, and/or videographic information (including CD or DVD based information) which reflect the visible color intensities related to various concentrations of metal ions and, thus, make it possible to correlate the metal ion concentration to the amount of hair damage.

The packaging and accompanying devices for any subject of the invention may be chosen and manufactured by persons skilled in the art on the basis of their general knowledge, and adapted according to the nature of the compositions to be packaged.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope of the invention.

Example 1

Sample Procedure for Determining the Amount of Damage to the Hair Based Upon the Amount of Metal Ion Attached to the Hair The Procedure Consists of the Following Steps:

A. Preparation of Standard Solutions

1. Prepare three standard solutions of nickel chloride at 1.0 μg/ml, 3.0 μg/ml, and 5.0 μg/ml, each solution containing 12 ml of nitric acid and water (qs), in a 100 ml volumetric flask.

2. Prepare another nickel chloride solution at 400 μg/ml in a Tris buffer solution, pH 7.0.

3. Prepare 100 ml of a blank solution containing 12 ml nitric acid and water (qs), in a 100 ml volumetric flask.

B. Treating Hair with the Nickel Chloride Solution

1. Weigh 0.20-0.50 g of dry hair into an erlenmeryer flask.

2. Fill the flask to the 50 mL mark with the Nickel Chloride Solution, swirl for a minute and then let stand for 60 minutes at room temperature.

3. After 60 minutes, discard the solution. Add 50 mL of Buffer Solution to the flask, swirl for a minute and let stand for 20 minutes. Discard the Buffer Solution. Repeat three times.

4. Add 50 mL of deionized water to the flask, swirl for a minute, let stand for 20 minutes, discard the water into the sink.

5. Place the flask with the hair into an oven and dry at 105-110° C. overnight.

6. Cool the samples in a dessicator to room temperature.

C. Digestion of the Samples

1. Weigh 0.10-0.30 g of hair sample in a microwave digestion vessel.

2. Add 6 mL of nitric acid in a fume hood.

3. Cap the vessel and tighten the venting screw.

4. Load the vessel(s) in the rotor in a symmetrical pattern.

5. Run the microwave oven using the conditions to allow complete dissolution of the hair sample.

6. Allow the vessels to cool to about 30° C. Transfer the rotor to the hood. Slowly loosen the vent screws to allow gases to escape. Remove the caps.

D. Dilution

1. Transfer the solution from each microwave digestion vessel into a 50 mL flask containing 10 mL of deionized water.

2. Rinse the vessel and the lid with deionized water not less than three times and transfer the washings to the same flask. Let the flask cool to room temperature.

3. Dilute to volume with deionized water and mix well. This is the Sample Solution. Make additional dilutions if the absorption reading is out of the calibration range. The final dilution should result in a concentration of nickel between 1.0 μg/mL and 5.0 μg/mL.

E. Sample Analysis by Atomic Absorption Spectroscopy (AAS)

1. Set up the Atomic Absorption (AA) spectrometer, a Perkin-Elmer Aanalyst 100 with an acetylene-compressed air flame, according to the instrument manufacturer's recommendations and adjust until the absorbance signal is maximized.

2. Autozero the absorbance reading using the Blank Solution.

3. Measure the absorbance of the Nickel Standards 1.0 μg/mL, 3.0 μg/mL, and 5.0 μg/mL.

4. Prepare a calibration curve based on these standards. The correlation coefficient should not be less than 0.999.

5. Aspirate each sample solution and record the measured concentration.

H. Calculation $$C_{Ni} = C_m \times \frac{V}{M} \times DF$$

where:
W=Sample weight, g
DF=Dilution factor (if needed)
    $C_{Ni}$=Concentration of nickel in hair, μg/g (ppm)
    $C_m$=Concentration of nickel in sample solution, μg/mL
    V=Volume of sample solution (50 mL)

Example 2

Analysis of Different Types of Hair

Samples of different types of hair were treated with 50 mL of 400 μg/mL nickel (II) chloride solution following the conditions in Example 1, in all cases using between 0.1 and 0.3 g of hair. Samples were then rinsed with three 50 ml portions of buffer and one portion of deionized water and dried according to the method above. All sample solutions were prepared in triplicate.

In some instances, samples were digested using the conditions described in Example 1. In other cases, an alternate digestion in open digestion vessels was employed. Samples were weighed in disposable polypropylene tubes; 6 ml of nitric acid were added to the tube. The tubes were placed into a MiniMod heating block from SPI international and heated at 90 C for about 30 minutes. After cooling to room temperature, the samples were transferred to a 50 ml volumetric flask, brought to volume with deionized water and analyzed by AAS as described in Example 1.

The different types of hair analyzed consisted of virgin medium brown hair, African-American hair, and 90% gray hair subjected to various treatments such as dyeing, permanent waving, bleaching or alkaline relaxation, and UV light-exposure. The hair swatches were 12 inches in length and the virgin medium brown hair samples (from DeMeo Brothers, New York) were determined to have an alkaline solubility (SA) value of 5.8%.

The amounts of Nickel ions absorbed by the hair samples were evaluated and compared to known values of alkaline solubility in order to validate the Nickle probe method. Alkaline solubility methods are well known as is illustrated by U.S. patent application 2004/0219121 and U.S. Pat. Nos. 6,022,836, 5,679,113 and 5,932,201, as well as Maillan, Business Briefing: Global Cosmetics Manufacturing 2004 (available at www.bbriefings.com).

Results

Bleached Hair

Figure 2:
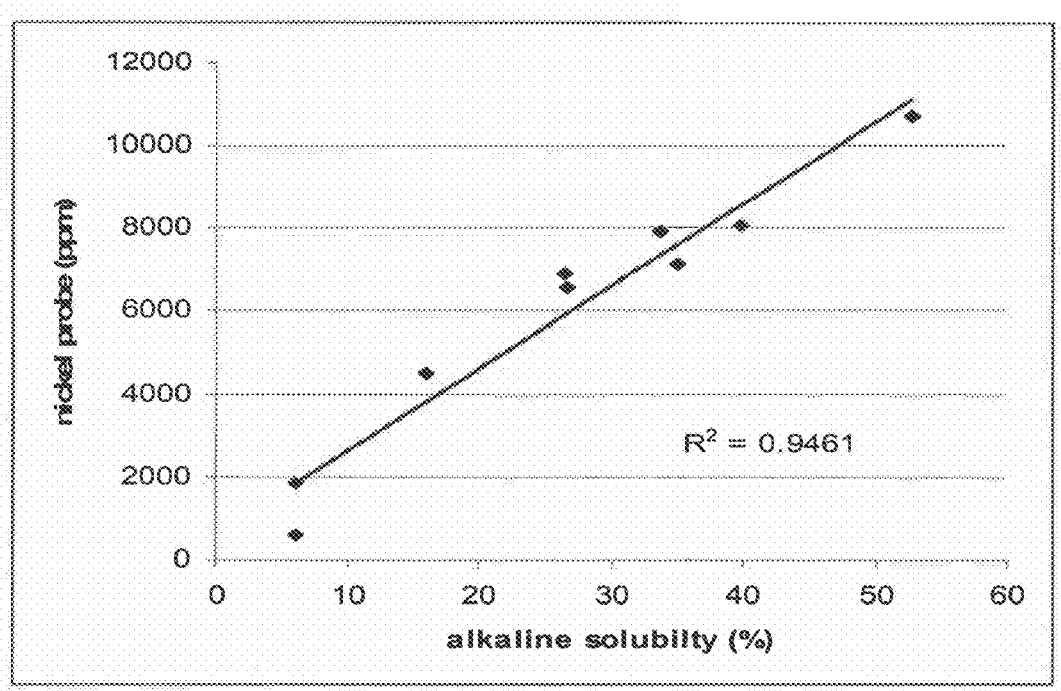
FIG. 2 plots the nickel probe measurements against the alkaline solubility values in Table 1.

A series of nine bleached Caucasian hair samples with known values of alkaline solubility were evaluated using the nickel probe method. The results from both methods are given in Table 1. An increasing value for alkaline solubility is an indication of increased hair damage. A strong linear correlation ($r^2 > 0.94$) is found when the results are plotted as shown in FIG. 2. Such a comparison indicates that the nickel probe method is effective in measuring the extent of hair damage in bleached Caucasian hair.

TABLE 1

Alkaline Solubility (% SA) and Nickel Probe Values for a Series of Bleached Caucasian Hair Samples

| Hair Sample ID | % SA | Ni Probe (ppm) |
|---|---|---|
| A | 6 | 587 |
| B | 16 | 4494 |
| C | 26.7 | 6562 |
| D | 35.1 | 7107 |
| E | 6.1 | 1870 |
| F | 26.4 | 6881 |
| G | 33.8 | 7906 |
| H | 39.8 | 8067 |
| I | 52.7 | 10680 |

Dyed Hair

Two different types of dyed hair were studied using the nickel probe method. One set of hair samples was prepared using 90% gray hair, to which four applications each of eleven different hair dye products were applied to separate samples.

The second series of dyed hair samples was prepared using the virgin medium brown hair which were subjected to either one or four applications of various hair dye products.

Figure 3:
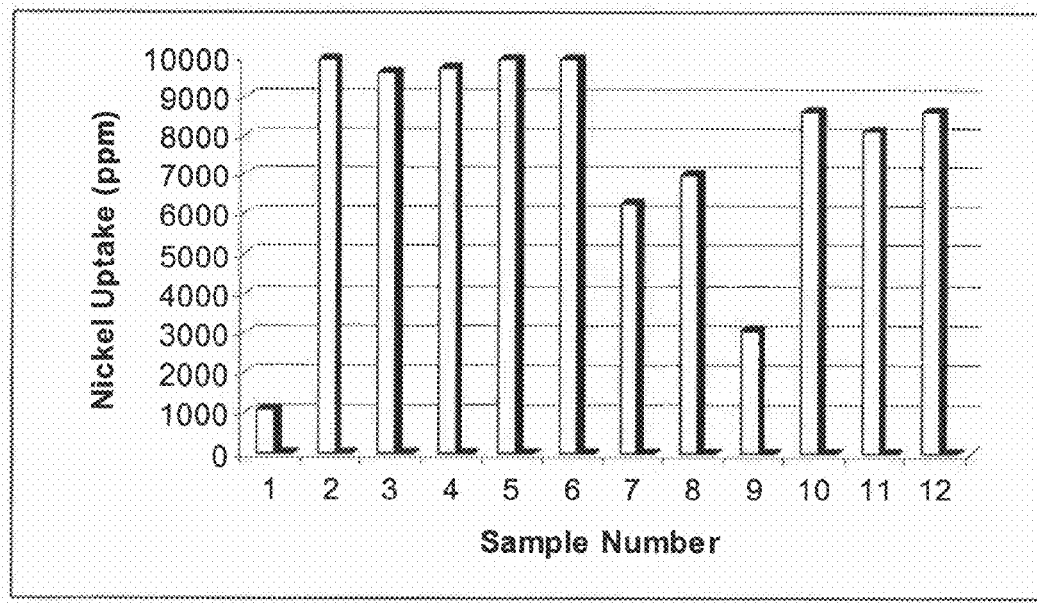
FIG. 3 shows the nickel uptake values (ppm) for the dyed gray Caucasian hair in Table 2.

Results of all measurements are also given in Tables 2 and 3, and graphically displayed in FIG. 3. All dyed samples can be readily distinguished from the untreated gray hair based on the amount of nickel found which supports the nickel probe method to evaluate the condition of hair after the dyeing process.

TABLE 2

Alkaline Solubility (SA %) and Nickel Uptake Values (ppm) for a Series of Dyed 90% Gray Caucasian Hair

| Hair Sample ID | SA % | Ni, ppm |
|---|---|---|
| (1) Untreated | — | 1078 |
| (2) | 73.9 | 9942 |
| (3) | 73.1 | 9644 |
| (4) | 60.5 | 9740 |
| (5) | 59.6 | 9950 |
| (6) | 65.8 | 9939 |
| (7) | 59.6 | 6265 |

TABLE 2-continued

Alkaline Solubility (SA %) and Nickel Uptake Values (ppm) for a Series of Dyed 90% Gray Caucasian Hair

| Hair Sample ID | SA % | Ni, ppm |
|---|---|---|
| (8) | 63.4 | 6989 |
| (9) | 37.5 | 3050 |
| (10) | 59.7 | 8634 |
| (11) | 62.6 | 8125 |
| (12) | 65.4 | 8639 |

The nickel probe method can be used to distinguish among various dyed samples. For example, the sample prepared using sample 9 has a much lower level of nickel uptake than any other sample, allowing it to be distinguished from samples prepared from any other product evaluated in this experiment. The nickel probe result is also consistent with the SA measurement for this sample, also showing a lower value than any other sample studied.

Thus, under the above conditions, there is a general correlation between the nickel probe results and the SA measurements (lowest NPM results match lowest SA results, higher results tend to match). while there is not a high degree of correlation found with the bleached virgin hair. a The linear correlation coefficient ($r^2$) for nickel uptake versus SA for the dyed gray hair samples is 0.6655. Some of the samples with higher SA values (60-65%) show lower values for nickel uptake. The nickel probe method appears to show better discrimination for certain types of samples than the SA method. Further, the SA results found for some of these samples are much higher than those found for the bleached hair study (maximum values 74% vs. 53% SA).

TABLE 3

Nickel Uptake Values for Samples of Dyed Medium Brown Caucasian Hair

| Hair Sample ID | Color | Applications | Ni, ppm |
|---|---|---|---|
| 1 - untreated | Untreated | Untreated | 751 |
| 2 | Ash/blue | 1× | 767 |
| 3 | Neutral | 1× | 991 |
| 4 | Red/copper | 1× | 999 |
| 5 | Neutral | 1× | 1148 |
| 6 | Ash/blue | 4× | 832 |
| 7 | Neutral | 4× | 1024 |
| 8 | Red/copper | 4× | 1210 |
| 9 | Neutral | 4× | 1469 |

In all cases, the dyed samples showed a greater uptake of nickel than did the untreated hair. Only the sample treated with the lightest shade (sample 2, Ash/blue) was not significantly different from the untreated hair. This was found for both the single application as well as for the sample treated four times. The samples treated with Ash/blue were significantly different from all other dyed samples, however. In fact, all shades could be distinguished from one another based on nickel uptake, except for the single application samples of 7 (neutral) and 8 (red/copper).

Results for the next darker color, sample 7, Neutral, showed a small increase in nickel uptake when the one and four application samples were compared. The moderate difference, however, was found to be not significant. For the darker shades, a significant difference was found between one and four applications.

This experiment supports the use of the nickel probe method to evaluate hair damage resulting from hair dyeing.

The method can distinguish between samples treated with different shades of hair dye as well as between the number of times a dye is applied. Darker shades of dye may lead to a greater extent of hair damage.

Permed Hair

The virgin medium brown hair was treated with three different permanent wave products. One treatment was used on each hair sample. A 90% gray hair sample was also treated with a permanent wave product.

The damage to hair caused by permanent wave treatment was explored using the nickel probe method and the results shown in Table 4. Significant differences were found between the untreated hair and treated hair. Further, the differences between any two of the permanent wave products used were also found to be significant. The extent of nickel uptake is consistent with the amount of damage expected from the treatment products. The product for FINE/LIMP hair is expected to be less harsh, and this result is seen in the nickel probe results.

In addition, the 90% gray hair was treated with another perm product (DULCIA VITAL) and samples evaluated before and after treatment. Again, a significant difference is found between untreated and treated hair.

TABLE 4

Nickel Uptake Values for Hair Subjected to Permanent Wave Treatment

| Technology | Perm | Ni, ppm |
|---|---|---|
| Untreated | No perm treatment | 751 |
| Ammonium Thioglycolate | Redken The Conditioned Curl Normal Formula | 3259 |
| Ammonium Thioglycolate | Vector Plus Extra Body Formula | 2189 |
| Glycerol Mono Thioglycolate (GMTG) | Creative Curl Fine/Limp Formula | 1755 |
| Untreated | Untreated (90% gray hair) | 1078 |
| Thio technology | Dulcia Vital: DV2 (on 90% gray hair) | 1734 |

Relaxed and Colored African-American Hair

African-American hair from various donors was used in two separate studies. In the first study, one lot of African-American hair was first relaxed with MIZANI Medium/Normal Lye Relaxer and then colored with three different dyeing products, Dye 1, Dye 2, and Dye 3. The hair treatments were conducted two separate times by the same staff member, resulting in samples indicated as Group 1 and Group 2.

The samples were analyzed using the nickel probe method and the results are shown in Table 5. The difference between the untreated hair and relaxed hair is clearly seen for both groups. Also seen are the differences in nickel uptake related to the various dyes. All differences are significant. The nickel probe method yields information to allow hair treated with different products to be differentiated

TABLE 5

Nickel Uptake Values for a Sample of Ethnic Hair after being Relaxed and Colored. Separate Treatments of Two Lots of the Same Hair Sample.

| | Nickel, ppm | |
|---|---|---|
| TREATMENT | Group 1 | Group 2 |
| Untreated - African American | 463 | 311 |

TABLE 5-continued

Nickel Uptake Values for a Sample of Ethnic Hair after being Relaxed and Colored. Separate Treatments of Two Lots of the Same Hair Sample.

| | Nickel, ppm | |
|---|---|---|
| TREATMENT | Group 1 | Group 2 |
| Relaxed | 4039 | 2574 |
| Relaxed + Dye 1 | 6959 | 4922 |
| Relaxed + Dye 2 | 5577 | 4638 |
| Relaxed + Dye 3 | 5959 | 4703 |

Of particular note in this study is the difference in results between Group 1 and Group 2. Although similar treatments yielded different results, the results show the same trend for untreated versus treated and among the different dyes evaluated. In addition, the data exhibit the same trend; the same samples show the highest and lowest values in each set. Intermediate values are consistent between data sets. There are, however, significant differences in the absolute values between the same samples treated in the two separate groups which could likely be attributed to the inherent variability in the natural hair sample, the variability in treating hair samples and the variability in the practice of the nickel probe method. All these factors must be considered in any study of the extent of damage to hair.

In a separate experiment, a different lot of African-American hair samples was relaxed and then colored three, six or nine times with specific dye products. This second study of African American hair was conducted, primarily to follow the differences in damage following an increasing number of dye treatments. The hair samples were relaxed using Motions Hair Relaxer Super Formula for Coarse/Resistant Hair and shampooed using Motions Neutralizing Shampoo distributed by Alberto-Culver. The dyes used to treat hair samples were a formula containing a polymer and oil (Composition D), a formula with oil but no polymer (Composition E), and a formula with no oil and no polymer (Composition E). One sample was subjected to the relaxer treatment only.

The 90% gray hair was also subjected to relaxation treatment using one application of SOFTSHEEN/CARSON Dark and Lovely Regular.

Figure 4:
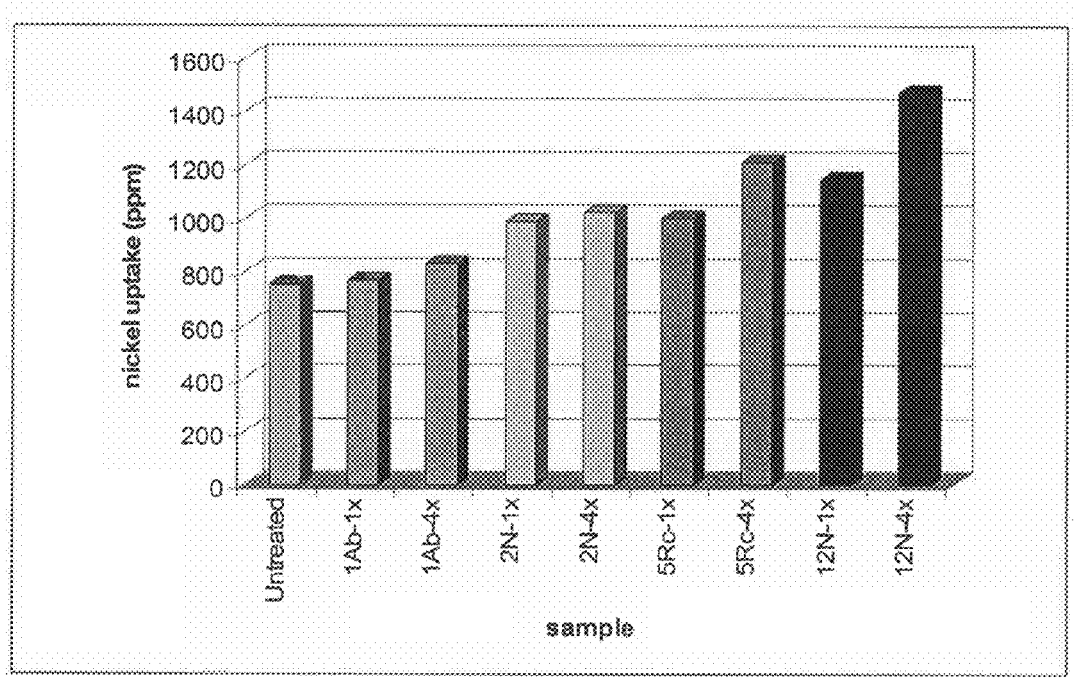
FIG. 4 shows the nickel uptake values for the samples of dyed medium brown Caucasian hair in Table 3.
Figure 5:
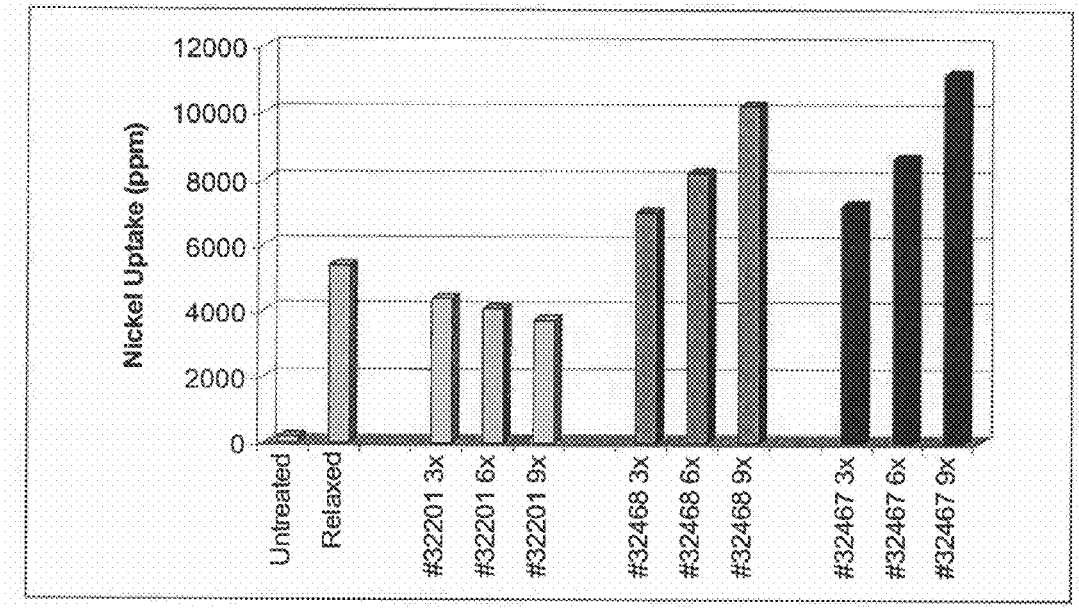
FIG. 5 shows the nickel uptake values for the samples of relaxed and colored ethnic hair in Table 6.

Results from the nickel probe method are given in Table 6 and shown graphically in FIG. 4. Alkaline solubility data was available for some samples and is also given in Table 6.

Treated samples were found to have significantly higher levels of nickel uptake than the untreated hair. Samples that were dyed following relaxing also had distinctly different levels of nickel uptake. For Composition F and Composition E, increasing the number of dye treatments resulted in an increase in the uptake of nickel. The results are consistent with the alkaline solubility measurements of the same samples compared with untreated hair.

TABLE 6

Nickel Uptake and some Alkaline Solubility Values for Relaxed and Colored Ethnic Hair

| Hair Type and Treatment | Ni, ppm | SA % |
|---|---|---|
| Untreated Ethnic | 215 | 6.5 |
| Relaxed | 5380 | — |
| Relaxed + Composition D 3x | 4384 | 21.7 |

TABLE 6-continued

Nickel Uptake and some Alkaline Solubility
Values for Relaxed and Colored Ethnic Hair

| Hair Type and Treatment | Ni, ppm | SA % |
|---|---|---|
| Relaxed + Composition D 6× | 4070 | — |
| Relaxed + Composition D 9× | 3717 | — |
| Relaxed + Composition E 3× | 7007 | 16.1 |
| Relaxed + Composition E 6× | 8200 | — |
| Relaxed + Composition E 9× | 10203 | — |
| Relaxed + Composition F 3× | 7213 | 16.2 |
| Relaxed + Composition F 6× | 8663 | — |
| Relaxed + Composition F 9× | 11180 | — |

Samples treated with Composition D showed lower overall nickel uptake values than other treatments and progressively lower values of nickel uptake as more applications were completed. All differences for these samples are significant. It may be that the composition of Composition D can have some effect to improve the quality of hair following treatment. Alternatively, the nickel uptake results are inconsistent with the alkaline solubility measurement of the sample treated three times with Composition D. This sample gave the highest value for alkaline solubility. Treatment with this formulation may block or hinder sites in the hair that would otherwise be available to bind nickel.

UV Light Exposed Hair

A sample of the virgin medium brown hair was subjected to exposure to UV light, to determine whether the nickel probe method could be used to evaluate any resulting damage. Both sides of a hair tress sample were exposed for 24 hours to 250 W/m$^2$ light in the SunTest XLS+apparatus from Atlas Material Testing Solutions, Inc. This is equivalent to 21.6 MJ/m$^2$, comparable to moderate sunlight exposure. The light exposed sample was found to contain 879 ppm nickel, compared with the level of 751 ppm found in the untreated hair. This difference is large enough to be significant. This outcome supports use of the nickel probe method to study hair damaged by exposure to light.

Example 3

The procedures set forth in the above example were followed for this example. 400 ppm solution of Ni was prepared in a tris buffer. DeMeo virgin hair was soaked for an hour in 20 mL of nickel solution. It was rinsed 6 times with a pH 7 buffer (20 minutes per rinse). The hair was dried overnight in an oven at 105C.

Virgin Hair Results—Bunsen Burner

Hair portions were weighed, transferred to test a tube and decomposed in 50% H2O2 with heat from a bunsen burner. Decomposition was partial. Result was a fine suspension. 5 drops of 0.1 N NaOH were added to bring pH to 4 to 5. Final volume of 10 mL was achieved by adding DI water. Several reflectoquant readings were made for each sample with different test strips. Most hair samples provided a meter reading of LO indicating that <10 ppm nickel was detected. However, one or two hair samples read 10 to 14 ppm.

Calculations

The nickel uptake in hair was presented as ppm. The calculation to convert the amount of nickel uptake in hair is as follows: (ppm reading from the test strip)×(volume: 10 mL)/weight of hair. Thus, a test strip reading of 50 ppm from a sample weight of 0.1 g would correspond to the following uptake of nickel in hair: 50 ppm×10 mL/0.1 g=5000 ppm nickel in hair.

Damaged Hair Results—Bunsen Burner

Process was repeated with severely damaged hair (50.9% alkaline solubility). The readings are as follows:

1. 0.1058 g→52,45,48 ppm. This corresponds to 4568 ppm on average.

2. 0.1038 g→71,76,82 ppm. This corresponds to 7354 ppm 3. 0.1240 g→111,107,98 ppm. This corresponds to 8495 ppm 4. 0.1010 g→77,74,75 ppm. This corresponds to 7459 ppm.

There was scatter in these results and sample 1 appeared to be an outlier. Nevertheless, differences in nickel uptake were easily detected between virgin hair and severely damaged hair.

Damaged Hair Results—Water Bath

The experiments in this example were repeated using a water bath (for ten minutes) instead of a Bunsen burner. The dried hair swatch was transferred to a test tube, 5 mL of 50% H$_2$O$_2$ added. The test tube with hair and peroxide was heated in boiling water for ten minutes. The test tube was removed and 5 drops of 0.5N NaOH added to get the pH to ~5.

The volume was brought to 10 mL with DI water and the nickel measured with a test strip/reflectance meter.

Also, hair swatches were removed from the nickel solution at intervals of 15 minutes, 30 minutes and 1 hour.

Further, rinse time was cut to 2 minutes per rinse for a total of 12 minutes. Hair was placed in a glass vial, 5 ml of tris buffer added, capped and inverted several times. The buffer was decanted and fresh buffer added. The rinse process was repeated 6 times.

| 15 minute Soak | |
|---|---|
| 0.104 g → E-2, 60, 58 ppm | 5673 ppm |
| 30 minute Soak | |
| 0.0984 g → 82, 82 ppm | 8435 ppm |
| 60 minute Soak | |
| 0.0954 g → E-2, 85, 86 ppm | 8910 ppm |

Results from the 30 and 60 minute soak in nickel solution were in substantial agreement.

Damaged Hair Results—Water Rinsing Solution

The above procedures can be repeated using a water rinsing solution.

What is claimed is:

1. A method for determining the amount of damage to hair comprising:
   (a) placing hair into a solution comprising at least one type of metal ion so that an amount of the metal ion is attached to the hair;
   (b) removing the hair from the solution;
   (c) determining the amount of metal ion attached to the hair after the amount of metal ion attached to the hair has been released by the digesting agent, wherein determining the amount of metal ion attached to the hair comprises treating the hair with a digesting agent in an amount sufficient to release the metal ion from the hair and determining the amount of metal ion released from the hair; and (d) determining the amount of damage to the hair based upon the amount of metal ion attached to the hair.

2. The method of claim 1, wherein the solution comprises at least one type of metal ion in the +2 charge state.

3. The method of claim 1, wherein the solution comprises nickel ions in the +2 charge state.

4. The method of claim 1, wherein the digesting agent is a reducing agent or an oxidizing agent.

5. The method of claim 1, wherein the digesting agent is an enzyme.

6. The method of claim 1, wherein the amount of metal ion released from the hair is determined by reacting the released metal ion with a dye to form a colored complex having an intensity and determining the intensity of the colored complex.

7. The method of claim 1, wherein the amount of metal ion released from the hair is determined by reacting the released metal ion with a test strip comprising a binding agent for the released metal ion to form a metal ion/binding agent complex and determining the amount of metal ion/binding agent complex on the test strip.

8. The method of claim 7, wherein the amount of metal ion/binding agent complex on the test strip is determined using a reflectometer.

9. The method of claim 7, wherein the amount of metal ion/binding agent complex on the test strip is determined visually.

10. A kit for analyzing hair comprising:
(a) a solution comprising at least one type of metal ion;
(b) a digesting agent in an amount sufficient to release the metal ion from hair after the metal ion has become attached to the hair when the hair is placed into the solution;
(c) means for determining the amount of metal ion attached to the hair; and
(d) means for determining the amount of damage to the hair based upon the amount of metal ion attached to the hair, the means comprising at least one correlation aid reflecting visible color intensities related to various concentrations of metal ions.

11. The kit according to claim 10, wherein the solution comprises at least one metal ion in the +2 charge state.

12. The kit according to claim 10, wherein the solution comprises nickel ions in the +2 charge state.

13. The kit according to claim 10, wherein the digesting agent is a reducing agent or an oxidizing agent.

14. The kit according to claim 10, wherein the digesting agent is an enzyme.

15. The kit according to claim 10, wherein the digesting agent is in a solution.

16. The kit according to claim 10, wherein the means for determining the amount of metal ion attached to the hair comprises a dye which forms, with the metal ion, a colored complex having an intensity.

17. The kit according to claim 10, wherein the means for determining the amount of metal ion attached to the hair comprises a test strip comprising a binding agent for the metal ion.

18. The kit according to claim 10, wherein the means for determining the amount of damage to the hair based upon the amount of metal ion attached to the hair comprises a reflectometer.

19. The kit according to claim 10, wherein the means for determining the amount of damage to the hair based upon the amount of metal ion attached to the hair comprises instructions for visually interpreting results reflecting the amount of metal ion attached to the hair.

20. The kit according to claim 10, wherein the digesting agent is an oxidizing agent and the means for determining the amount of metal ion attached to the hair comprises a reflectometer and a test strip comprising a binding agent for the metal ion.

21. The kit according to claim 20, further comprising at least one test tube.

* * * * *

UNITED STATES PATENT AND TRADEMARK OFFICE
CERTIFICATE OF CORRECTION

PATENT NO. : 7,749,763 B2  Page 1 of 1
APPLICATION NO. : 12/057676
DATED : July 6, 2010
INVENTOR(S) : Gregory Shmuylovich et al.

It is certified that error appears in the above-identified patent and that said Letters Patent is hereby corrected as shown below:

Column 16, lines 64 and 65, delete "after the amount of metal ion attached to the hair has been released by the digesting agent".

Column 17, line 38, after the word "hair" insert --after the amount of metal ion attached to the hair has been released by the digesting agent--.

Signed and Sealed this

Ninth Day of November, 2010

David J. Kappos
*Director of the United States Patent and Trademark Office*